(12) United States Patent
Martens et al.

(10) Patent No.: US 9,095,698 B2
(45) Date of Patent: Aug. 4, 2015

(54) HIGH RESOLUTION ELECTRICAL STIMULATION LEADS

(75) Inventors: Hubert Cécile François Martens, Eindhoven (NL); Michel Marcel Jose Decré, Eindhoven (NL); Emil-Codrut Toader, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 27 days.

(21) Appl. No.: 13/517,473

(22) PCT Filed: Dec. 21, 2010

(86) PCT No.: PCT/IB2010/055975
§ 371 (c)(1),
(2), (4) Date: Jul. 19, 2012

(87) PCT Pub. No.: WO2011/077368
PCT Pub. Date: Jun. 30, 2011

(65) Prior Publication Data
US 2012/0277821 A1    Nov. 1, 2012

(30) Foreign Application Priority Data
Dec. 23, 2009 (EP) .................................. 09180684

(51) Int. Cl.
*A61N 1/36* (2006.01)
*A61N 1/05* (2006.01)

(52) U.S. Cl.
CPC .......... *A61N 1/0534* (2013.01); *A61N 1/36082* (2013.01); *A61N 1/36182* (2013.01); *A61N 1/36185* (2013.01)

(58) Field of Classification Search
CPC ............ A61N 1/3605; A61N 1/36128; A61N 1/3615; A61N 1/36182; A61N 1/36185; A61N 1/0534; A61N 1/36082
USPC ............................... 607/45, 74, 115, 116, 117
See application file for complete search history.

(56) References Cited

U.S. PATENT DOCUMENTS

| | | | |
|---|---|---|---|
| 6,393,325 B1 | 5/2002 | Mann et al. | |
| 2001/0034542 A1 | 10/2001 | Mann | |
| 2003/0195582 A1 | 10/2003 | Mann | |
| 2004/0034394 A1* | 2/2004 | Woods et al. | 607/46 |
| 2004/0215287 A1 | 10/2004 | Swoyer et al. | |
| 2008/0215125 A1 | 9/2008 | Farah et al. | |

OTHER PUBLICATIONS

International Search Report and Written Opinion for PCT/IB2010/055975 dated May 31, 2011.
Official Action dated Apr. 15, 2014 for European Patent Application No. 10 812 935.4.

\* cited by examiner

*Primary Examiner* — Allen Porter, Jr.
(74) *Attorney, Agent, or Firm* — Shumaker & Sieffert, P.A.

(57) ABSTRACT

System for providing a stimulus comprising a probe with multiple electrodes each capable of providing a particular current to surrounding tissue a generator for providing to each of the electrodes the particular current a controller for controlling the generator to provide current to the electrodes to achieve a desired electrical field around the probe.

13 Claims, 7 Drawing Sheets

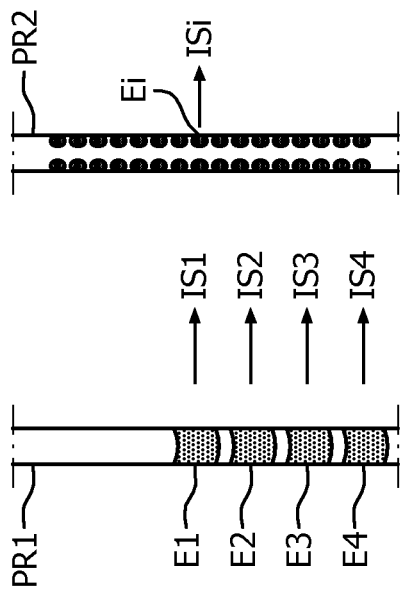
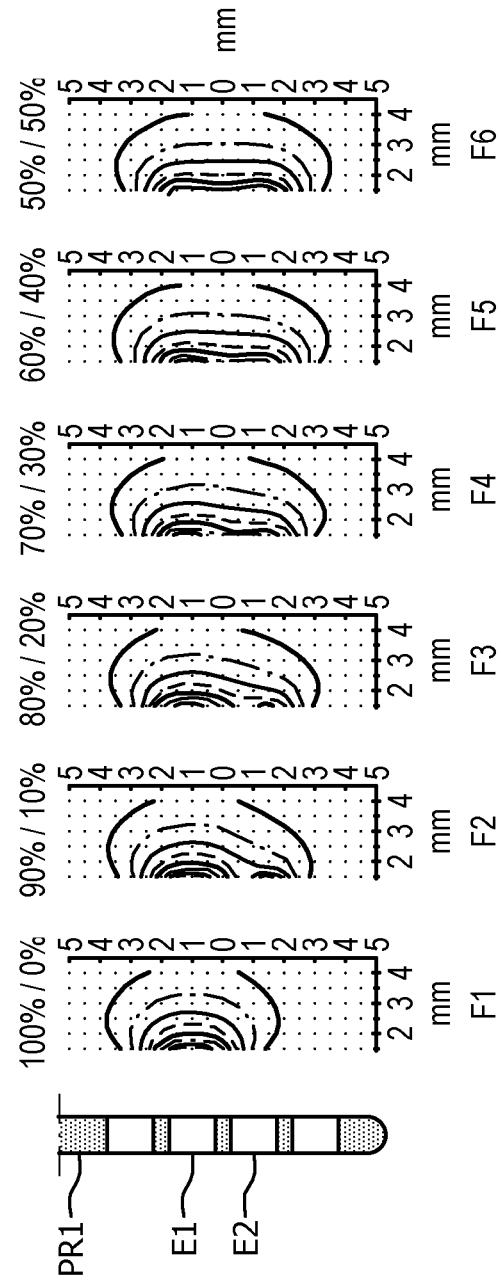
FIG. 1A
FIG. 1B
FIG. 2

HIGH RESOLUTION ELECTRICAL STIMULATION LEADS

CROSS-REFERENCE TO RELATED APPLICATIONS

This application is a U.S. National Stage of International Patent Application No. PCT/IB2010/055975 filed on Dec. 21, 2010, which claims priority to European Patent Application No. 09180684.4 filed on Dec. 23, 2009, both of which are incorporated herein by reference in their entirety.

FIELD OF THE INVENTION

The invention relates to a system for providing an electrical stimulus to surrounding tissue, and a method of providing an electrical stimulus to surrounding tissue.

BACKGROUND OF THE INVENTION

New high resolution neural interfaces allow for accurate spatial steering of therapeutic stimulation towards target tissue. Such high-resolution interfaces usually comprise an array-like distribution of elements (e.g. contacts or electrodes) capable of delivering stimuli (e.g. electrical pulses) and the array is usually placed on a carrier structure (e.g. an elongated flexible probe). FIG. 1B presents an example of such a high resolution neural interface used for the accurate delivery of electrical stimulation for the purpose of deep brain stimulation therapy. For comparison is provided in FIG. 1A on the same scale a conventional low-resolution neural interface for deep brain stimulation therapy. The electrodes shown in FIGS. 1A and 1B are also referred to as state of the art DBS lead and high resolution DBS array, respectively. It has to be noted that such a generation of a field in a tissue may also be useful in other applications such as ablation of tissue or even non-therapeutic applications.

The electrical potential in the brain tissue surrounding the DBS leads can be computed using the finite element method (FEM) as disclosed in Edsberg L., Introduction to Computation and Modeling for Differential Equations, J. Wiley, Wiley-Interscience: pp. 140-146, 2008, ISBN-13 9780470270851.

The electric potential V generated by the DBS electrodes is obtained by solving Poisson's equation as is disclosed in Bronzino J., Biomedical Engineering Handbook 2006, vol. I, section III, chapter 20, pp. 1-3, CRC. 1, ISBN-13 9780849304613:

$$\nabla^2 V = \frac{1}{\sigma} \nabla \cdot \vec{J}^i, \quad (1)$$

where $\nabla^2$ is the Laplace operator, $\vec{J}^i$ is the current source and $\sigma$ the electrical conductivity.

For estimation of DBS activation volumes one can compute the activating function (AF). In general, the AF quantifies the driving force for depolarization of neuronal elements as is disclosed in Rattay F., The basic mechanism for the electrical stimulation of the nervous system, Neuroscience Vol. 89, No. 2, pp. 335-346, 1999.

As disclosed in McIntyre C. C., S. Mori, et al., Electric field and stimulating influence generated by deep brain stimulation of the subthalamic nucleus, Clinical Neurophysiology Volume 115 Issue 3, pp. 589-595, March 2004, estimation of the stimulation volumes is realized by thresholding the activation function distributions, which has been shown to provide a good initial estimate of the volume of activated tissue which is computed with more extensive computational modeling. The activation function is obtained by taking the discretized second spatial derivative of the external potential. For example for elements oriented in the z-direction, the activation function is computed as:

$$AF_z(x,y,z)=V(x,y,z-\Delta z)+V(x,y,z+\Delta z)-2V(x,y,z), \quad (2)$$

wherein the step length $\Delta z=0.5$ mm is the typical internode length for myelinated fibers. Activation occurs when the activation function crosses a certain threshold that is i.e. dependent on stimulation parameters (most notably pulse duration), fiber properties and relative fiber-electrode orientation.

In clinical practice, repositioning of stimulation fields will be considered when for a given stimulation configuration adverse side-effects are obtained. By steering the stimulation fields away from areas responsible for such side-effects one will try to avoid side-effects and simultaneously keep good therapeutic effects. In current clinical practice the usual method for displacing stimulation fields is by selecting a different contact for stimulus delivery. As this immediately displaces stimulation fields by 2-3 mm this is a quite coarse method. More fine control of stimulation field displacement can be achieved by current steering techniques and/or higher-resolution stimulation arrays.

Current steering is known in the art as a method to displace stimulation fields. In brief, the method consists of balancing current delivery between two or more contacts. For example, Butson, C. R. and McIntyre C. C., Current steering to control the volume of tissue activated during deep brain stimulation, Brain Stimulation 1(1): pp. 7-15, 2008, demonstrate how current steering can be used with a state-of-the-art DBS lead to tune the stimulation volumes, see FIG. 2. In this example, a total stimulation current is distributed over two adjacent electrodes and depending on the balance of current between the two electrodes a different activation profile results. FIG. 2 shows from left to right: a DBS electrode, a series of field contours starting from activation of a single electrode and ending with the activation of two neighboring electrodes of the DBS electrode. As is clear from FIG. 2, balancing the current between two contacts allows shifting the activation volume.

US 2007/0203539 discloses current steering with the high resolution DBS-array which is shown in FIG. 1B.

SUMMARY OF THE INVENTION

It is an object of the invention to enable easily applying field steering in systems with high resolution probes. In particular, it is an object of the invention to provide a system and a method applying current steering with high resolution probes without unduly increasing the power consumed.

A first aspect of the invention provides a system for providing an electrical stimulus to surrounding tissue as claimed in claim 1. A second aspect of the invention provides a method of generating an electrical stimulus for application to surrounding tissue with a probe with multiple electrodes as claimed in claim 13. Advantageous embodiments are defined in the dependent claims.

A system for providing an electrical stimulus to surrounding tissue in accordance with the first aspect of the invention comprises a probe with multiple electrodes. A generator supplies electrical signals to the electrodes to obtain a field distribution in the surrounding tissue. A controller which controls the generator provides in a first state a first distribution of the electrical signals to the electrodes to generate a first field distribution, and in a second state a second distribution of the electrical signals to the electrodes to generate a second field distribution. The first distribution of electrical signals is more symmetrical with respect to the electrodes than the second distribution of electrical signals, and a total amount of electrical stimulation currents caused by the electrical signals in the second state is lower than in the first state. By having a total amount of currents which is less in a more asymmetrical distribution, it is possible to prevent a too large increase of the power drawn by the system. Especially if the power to the system is supplied by a battery, a too large power drain would cause a battery to be depleted too fast. The other way around, if the distribution of the electrical signals is selected to be more symmetric or is changed into a more symmetric distribution, it is allowed to increase the total amount of currents without causing the battery to be drained too fast.

The most symmetrical distribution of electrical signals with respect to the electrodes is obtained if the activation of the electrodes is mutually identical, for example by supplying identical currents to all the electrodes of the array of electrodes. In this manner, this symmetry of the distribution can be defined independent from the actual shape of the array of electrodes. The resulting shape of the field distribution depends on the actual shape of the array. As soon as the electrical signals activating the electrodes are different, the distribution of the electrical signals is called asymmetric. The more the activation of the electrodes differs, the more asymmetric this distribution of electrical signals will be and the more the resulting field distribution deviates from the field occurring during the symmetrical distribution of the electrical signals.

In the same manner, with symmetrical field distribution (with respect to the electrodes) is meant in this context the field distribution which is obtained when all electrodes are activated mutually identically. The resulting field distribution has a shape which is determined by the shape of the array of electrodes. If the probe of FIG. 1B is used the field will be truly rotational symmetric if all currents supplied to the electrodes are identical. By not activating all electrodes mutually identically, for example by supplying a different current to at least one of the electrodes, the shape of the generated field deviates from the shape obtained by mutually equal activation and is called to be less symmetric. Such an unequal activation may result in a change with respect to the original symmetric field to obtain a directivity of the field in a particular direction. Further, also situations wherein a part of the electrodes is not activated at all are considered to be less symmetric. For example, with respect to the probe shown in FIG. 1B, also situations wherein rings of electrodes are not activated are a more asymmetrical distribution which leads to a more asymmetrical field distribution. In all the situations wherein the symmetry of the distribution of the electrical signals, or the symmetry of the field with respect to the shape of the electrode array, becomes less, the total current supplied to the electrode array should be reduced.

In an embodiment, the controller adjusts the electrical signals supplied to the electrodes such that the generated field gradually changes from the first distribution in the first state into the second distribution in the second state. By gradually changing the field distribution when the probe is positioned in the tissue, possible undesirable side effects are minimized. If the field distribution changes too fast, the patient has no possibility to indicate in time that the change is unacceptable.

In an embodiment, the controller reduces the total amount of electrical stimulation currents when changing from the first state into the second state in such a manner that the total power supplied to the electrodes in the first state and in the second state is kept substantially constant. In this manner, the power drawn from the battery is kept substantially constant and an undesirable fast depletion of the battery is prevented. For example, dependent on the desired life time of the battery, the current may not be allowed to increase more than 25% or even not more than 5%.

In an embodiment, the controller reduces the total amount of electrical stimulation currents to keep the field distribution in the second state within borders of the field distribution in the first state. In another embodiment, the controller reduces the total amount of electrical stimulation currents such that a maximum of the field distribution in the second state is substantially equal to a maximum of the field distribution in the first state. The maximum of the field distribution is defined by trespassing a particular threshold of the field strength. Thus, the electrical stimulation currents are controlled in such a way that the strength of the field in the second state is nowhere larger than the strength of the field in the first state, only the directivity changes.

In an embodiment, the controller generates in the first state a field distribution which is symmetrical around the probe and in the second state a field distribution which has a directivity extending in a desired direction with respect to the probe.

In an embodiment, the first field distribution and the second field distribution are distributions of a voltage field, an electrical field, an activating function, or an activation-profile of multi compartment neuronal models.

In an embodiment, the probe has an elongated shape and the multiple electrodes are circumferentially arranged on the probe at different axial positions, wherein several electrodes are present at a same one of the different axial positions. Such a high resolution DBS probe appears to be especially suited to be placed in tissue and to generate a desired field distribution with a high accuracy.

These and other aspects of the invention are apparent from and will be elucidated with reference to the embodiments described hereinafter.

BRIEF DESCRIPTION OF THE DRAWINGS

In the drawings:

FIG. 1A shows a state-of-the-art low resolution DBS lead, and FIG. 1B shows a state-of-the-art high-resolution DBS-array, FIG. 2 shows constant-total-current field steering according to state-of-the-art which is illustrated with AF contours for the low resolution DBS lead.

Figure 3:
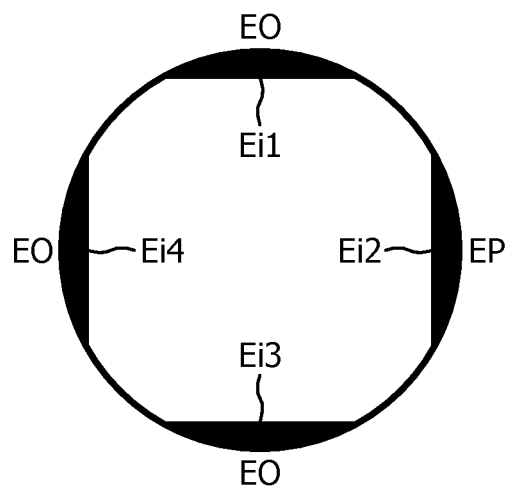
FIG. 3 shows a top view of the probe sketched in FIG. 1B with an indication of one 'preferred' and three 'other' directions.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION

FIG. 1A shows a state-of-the-art low resolution DBS lead, and FIG. 1B shows a state-of-the-art high-resolution DBS-array. Both DBS probes are elongated cylindrical support structures on which the electrodes Ei are indicated by black areas.

In FIG. 1A, of the low resolution DBS lead PR1, four electrodes E1 to E4 are shown which are arranged circumferential on the support structure. The low resolution DBS lead PR1 may have fewer or more than four electrodes E1 to E4. When driven, these electrodes E1 to E4 supply electrical stimulation currents IS1 to IS4, respectively to the surrounding tissue. The electrodes are collectively also referred to by Ei and the electrical stimulation currents are collectively also referred to by ISi.

In FIG. 1B, a high resolution DBS-array PR2 is shown in which groups of four electrodes Ei are axially displaced along the support structure. The four electrodes Ei are equidistantly positioned around the circumference of the support structure. However any other distribution of the electrodes Ei may be used. For example, the electrodes Ei in one group may be fewer or more than four and/or may be positioned in a non-equidistant manner. The number of electrodes Ei in the groups may differ. The distances between groups may be different. The support structure may have any suitable shape. In the following, the electrodes Ei are also referred to as the elements Ei.

The high number of elements Ei of the high-resolution DBS-array PR2 implies that an enormous number of stimulus-delivery combinations can be generated. Testing all these combinations is practically impossible. By making use of the current steering methods known in the art for electrodes Ei arranged along the length of the probe PR2, the problem can be greatly simplified. One way of employing the steering functionality of the high-resolution interface is by gradually shifting the total stimulus current towards a preferred direction with respect to the circumference of the probe PR2. One or more stimulation elements Ei (i.e. electrodes arranged along the circumference) are defined as 'preferred' direction and one or more elements Ei are defined as 'other' direction. Preferably, the 'preferred' and 'other' elements together comprise a symmetric arrangement, e.g. covering a circumference of a cylindrical probe PR2.

FIG. 2 shows constant-total-current field steering according to state-of-the-art which is illustrated with AF contours for the low resolution DBS lead. FIG. 2 shows from left to right: a DBS electrode PR1 and a series of field contours F1 to F6 for different ratios of steering currents on the electrodes E1 and E2. The ratio of steering currents for the electrodes E1 and E2 is indicated on top of the field contours. The total summed amount of steering currents is kept constant. F1 shows the field contours for the activation of the single electrode E1 and F6 shows the field contours when both electrodes E1 and E2 are equally activated. In this example, a total stimulation current is distributed over two adjacent electrodes E1 and E2. Depending on the balance of currents supplied to the two electrodes E1 and E2 a different activation profile results and thus shifts the activation volume.

FIG. 3 shows a top view of the probe sketched in FIG. 1B with an indication of one 'preferred' and three 'other' directions. FIG. 3 provides an axial top view of such an arrangement for the case of a square array of elements Ei like the example of FIG. 1B; there is one 'preferred' direction PD indicated and three 'other' directions OD. The array of elements may have any other suitable arrangement of the elements Ei dependent on the desired field distribution.

Following the current-steering techniques, we can formally implement current-steering as follows:

We apply a total stimulation current $I_{nominal}$ to the tissue adjacent the stimulation elements Ei that gets distributed over $n_{other}$ 'other' elements EO and $n_{pref}$ 'preferential' elements EP making a total of $n_{total}$ elements Ei being used for stimulus delivery.

In symmetric (non-steered) mode the 'other' and 'preferential' elements each receive (on average) a current $$i_{other} = i_{pref} = I_{nominal}/n_{total} \quad (3)$$

We define a current-steering balance parameter β that quantifies the asymmetry of the stimulation delivery such that each 'preferential' element EP receives (on average) a current $$i_{pref} = I_{nominal}/n_{total} * (1 + \beta * (n_{other}/n_{pref})) \quad (4)$$

and each 'other' element EO receives (on average) a current $$i_{other} = I_{nominal}/n_{total} * (1 - \beta) \quad (5)$$

As a result the total current delivered $n_{other}*i_{other} + n_{pref}*i_{pref} = I_{nominal}$ stays constant, but the current delivery profile gets gradually shifted by increasing the current-steering balance parameter β from 0 to 1 from a symmetric arrangement to a situation where all current gets imposed on the 'preferential' sites EP. Also possible is the case the current-steering balance parameter β>1, i.e. when an opposite polarity current is fed to the 'other' sites EO, leading to further displacements of the stimulation volumes. Note that the example taken from Butson and McIntyre 2008 (mentioned earlier) corresponds to a case of $n_{other} = n_{pref} = 1$.

Figure 4:
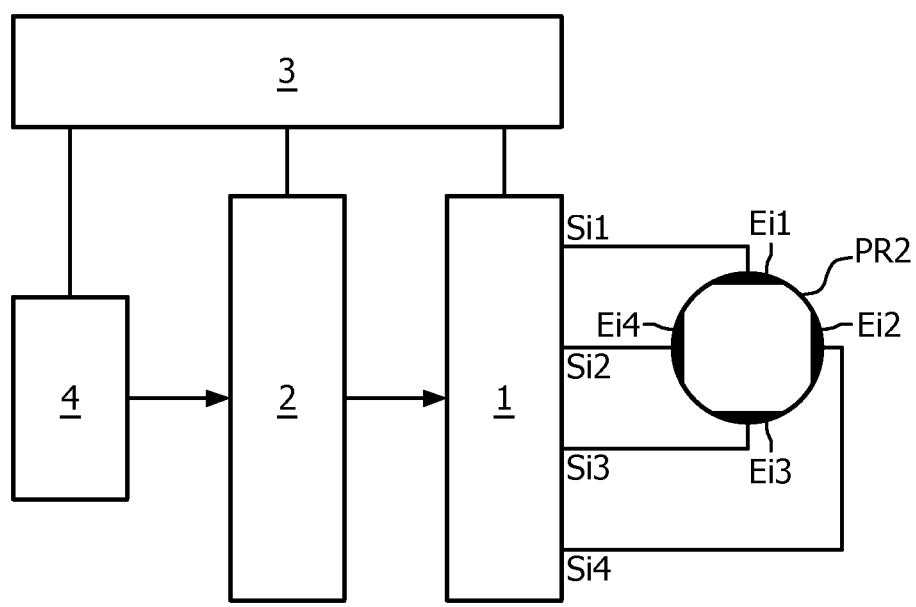
FIG. 4 shows a schematic block diagram of a system for generating electrical signals which are supplied to the electrodes of the probe shown in FIG. 3, FIGS. 5A and 5B show that the high-resolution DBS-array allows using field-steering techniques to accurately position stimulation fields with respect to the tissue.

FIG. 4 shows a schematic block diagram of a system for generating electrical signals which are supplied to the electrodes of the probe shown in FIG. 3. The generator 1 supplies electrical signals Si1 to Si4 (collectively referred to as Si) to the electrodes Ei of the high-resolution DBS-array shown in FIGS. 1B and 3. The controller 2 controls the generator 1 to supply a particular distribution of the electrical signals Si to the electrodes Ei to obtain a desired field distribution Fi in the tissue. A power source 3 supplies power to the generator 1 and the controller 2. A user interface 4 receives user input to the controller to enable input of a desired field distribution Fi, or a desired change of an existing field distribution Fi. For example, the user may indicate a change of the directivity of the field distribution Fi. If the patient with the implanted electrode is not in a clinical environment, this power source 3 is a battery. It is important that the battery can be used for a well-defined period of time. It is therefore very cumbersome if the battery is depleted within this period of time. Furthermore, it is advantageous to consume little power in general. When changing the generated field to become more asymmetrical the electrical signals Si have to be changed such that one of them becomes larger such that the current in the tissue in the direction of the asymmetry becomes larger. This increases the power consumption. In one aspect of the present invention, the total current generated in the tissue is decreased when the asymmetry of the field is increased. In an embodiment, the electrical signals Si are changed such that the power supplied to the tissue and thus the power requested from the battery 3 is kept substantially constant when the directivity of the field Fi is changed.

Figure 5A:
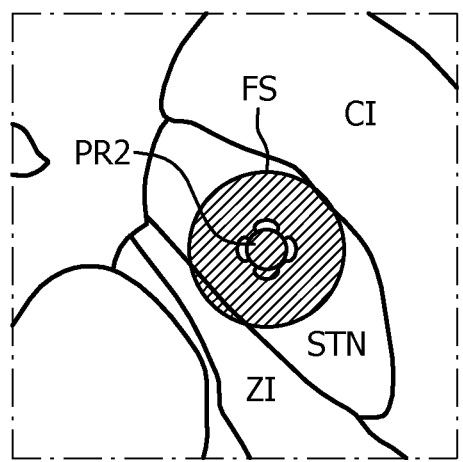
Figure 5B:
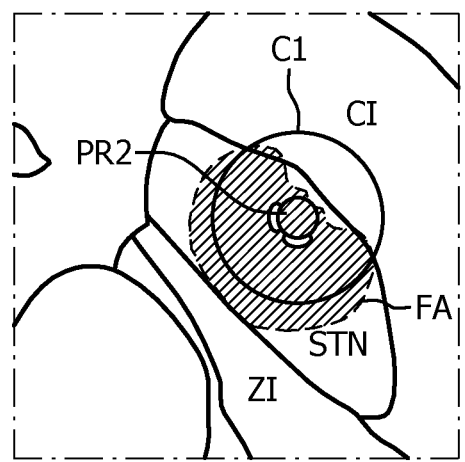

FIGS. 5A and 5B show that the high-resolution DBS-array allows using field-steering techniques to accurately position stimulation fields Fi with respect to the tissue. By the combination of current-steering with the high-resolution lead PR2 one can employ very accurate stimulation steering. For example, steering can be performed such that one can compensate for the case where symmetric delivery of stimulation would result in side-effects, e.g. because stimulation in a particular direction/region activates structures that may lead to adverse and unwanted side-effects. By having the option to steer stimulation, one may avoid the delivery of unwanted stimulation to those structures.

FIG. 5A shows an optimally placed probe PR2 in the middle of the area STN which is used in symmetric stimulation mode to obtain good target coverage resulting in the symmetrical field distribution indicated by FS. An equal result would be achieved with a state-of-the-art probe PR1. FIG. 5B shows that for a sub-optimally place probe PR2, the area STN can be covered well if applying field-steering techniques such that the area FA within the dashed line is covered. With the state-of-the-art probe PR1 such result cannot be achieved because such probe covers the area within the circle C1 and a sub-optimal target coverage and/or leakage into adjacent structures C1 occurs.

Figure 6C:
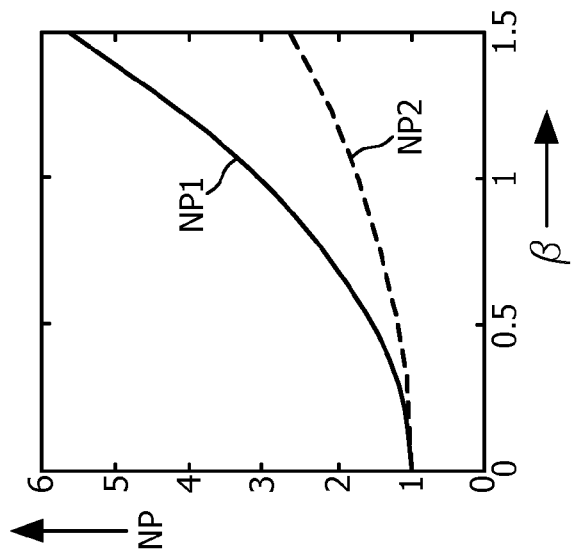
FIG. 6C shows a graph of the power consumption for the current-steering examples of FIGS. 6A and 6B, FIGS. 7A and 7B show effects of current-steering on the AF-profile if current limiting is applied.
Figure 6B:
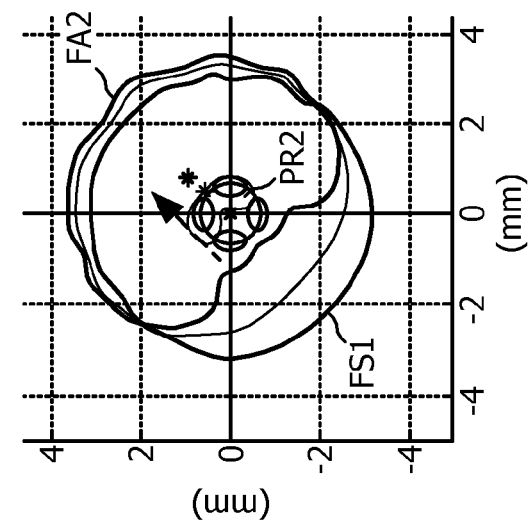
FIGS. 6A and 6B show effects of field-steering on the AF-profile during constant summed total current.
Figure 6A:
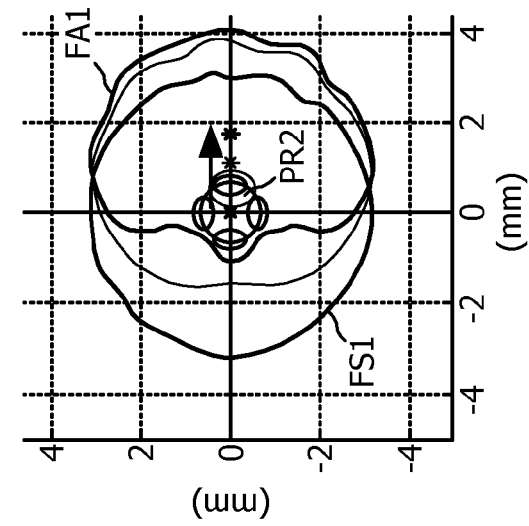

FIGS. 6A and 6B show effects of field-steering on the AF-profile during constant summed total current, and FIG. 6C shows a graph of the power consumption for the current-steering examples of FIGS. 6A and 6B. Both FIG. 6A and FIG. 6B show field distributions in a two-dimensional xy plane perpendicular to the axis of the probe PR2 of which the cross section is shown in FIG. 3. FIG. 6A shows a symmetrical field distribution FS1 which is changed into a field distribution FA1 with orthogonal directivity along the x-axis as is indicated by the arrow. FIG. 6B shows the symmetrical field distribution FS1 which is changed into a field distribution FA2 with directivity in the diagonal direction as is indicated by the arrow. FIG. 6C shows a graph of the normalized power consumption as function of the current-steering balance parameter $\beta$ for the current-steering examples of FIG. 6A in the line NP1 and of FIG. 6B in the dashed line NP2.

With increasing current-steering balance parameter $\beta$ according to above equations (4) and (5), the stimulation region is moved gradually away from the 'other' directions and simultaneously it is displaced into the 'preferential' directions indicated by the arrow. Further, with increasing steering (increasing $\beta$) the power consumption of the system strongly rises.

Thus, the above current steering shows the following effects:
  (a) Power consumption increases strongly when applying conventional current-steering,
  (b) Spread of stimulation increases into the preferred direction.

Effect (a) should be mitigated because increased power consumption negatively affects battery operation time of a stimulation device. However, also effect (b) should be mitigated because steering will be applied to reduce side-effects for a given setting and increased spread in a particular direction does bring the risk of unwanted excitation of another structure, potentially introducing other/new side-effects. See for example FIG. 5B, there the current-steering moved the field away from area CI (capsula interna), but simultaneously resulted in a shift of spread into the area ZI, which may be unwanted.

Therefore, the invention seeks to provide a system and a method for stimulation-field steering reducing power-consumption and/or being less prone to displacement of stimulation field spread.

According to the invention, the system for providing an electrical stimulus to surrounding tissue comprises a probe with multiple electrodes. A generator provides electrical signals to the electrodes to obtain a field distribution in the surrounding tissue. A controller controls the generator such that in a first state a first distribution of the electrical signals is applied to the electrodes to generate a first field distribution, and in a second state a second distribution of the electrical signals is applied to the electrodes to generate a second field distribution. The first field distribution is more symmetrical than the second field distribution, and a total amount of electrical stimulation currents caused by the electrical signals in the second state is lower than in the first state.

By decreasing the total amount of electrical stimulation currents in the tissue when the field distribution in the tissue is made less symmetrical, the negative effects shown in FIGS. 6A, 6B and 6C are mitigated. If the total amount of currents decreases for less symmetric fields, the power increase will be less or even may be kept constant and also the spread will be less. The total amount of currents may even be controlled such that the volume covered by the asymmetric field is maximal but still within the boundaries of the volume covered when applying the symmetric field. Thus, the invention provides a system with a stimulation-field steering function, wherein the stimulation field steering is achieved by changing the balance in current delivered between groups of stimulation elements ('steering') and whereby for increasing 'unbalance' the total current being delivered is automatically reduced according to a suitable algorithm.

For the case of two groups of stimulation elements Ei as discussed above, this can be formalized as follows:

Each 'preferential' element EP receives (on average) a current $$i_{pref} = I_{nominal}/n_{total} * (1 + f(\beta) * \beta * (n_{other}/n_{pref})) \quad (6)$$

and each 'other' element EO receives (on average) a current $$i_{other} = I_{nominal}/n_{total} * (1 - \beta) \quad (7)$$

where the function $0 \leq f(\beta) < 1$. So, $f(\beta)$ is a function to adjust the current level after the currents have been redistributed by applying the current-steering balance parameter $\beta$. For some applications, $f(\beta)$ may be a constant while for other applications $f(\beta)$ may indeed be a function of the current-steering balance parameter $\beta$. In an alternative representation, the above can be written as follows:

Each 'preferential' element EP receives (on average) a current $$i_{pref} = g(\beta) * I_{nominal}/n_{total} * (1 + \beta * (n_{other}/n_{pref})) \quad (8)$$

and each 'other' element EO receives (on average) a current $$i_{other} = g(\beta) * I_{nominal}/n_{total} * (1 - \beta) \quad (9)$$

wherein the function $g(\beta) < 1$. Here, $g(\beta)$ performs the function of adjusting the current level as $f(\beta)$ does above.

The function $f(\beta)$ can be optimized for different requirements, e.g. constant power consumption, or constant range of stimulus delivery in preferential direction, etc. Note that the case $f(\beta) = 0$ implies constant current being delivered to the preferential sites EP (also referred to as elements or electrodes) irrespective steering parameters.

In the above examples, it is not essential for the invention that all preferential elements EP receive a same current, and also not that all other elements EO receive a same current. The current distribution may be selected optimally in relation to the desired directivity of the field Fi to be generated.

By way of example of the aspects of the invention, a number of embodiments are provided below.

Figure 7C:
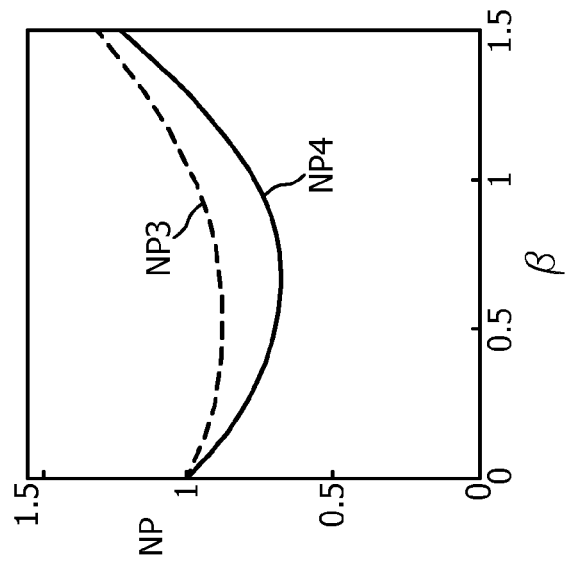
FIG. 7C shows a graph of the power consumption for the current-steering examples of FIGS. 7A and 7B, FIGS. 8A and 8B elucidate the spread of a field distribution.
Figure 7B:
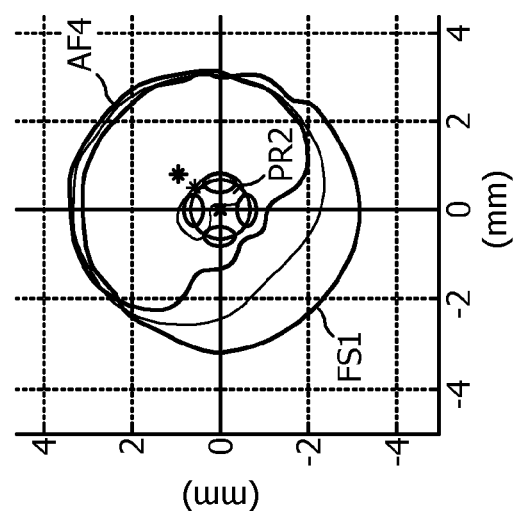
Figure 7A:
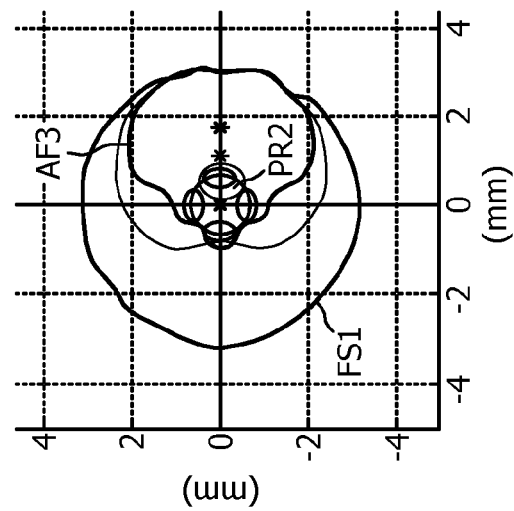

FIGS. 7A and 7B show effects of current-steering on the AF-profile if current limiting is applied, and FIG. 7C shows a graph of the power consumption for the current-steering examples of FIGS. 7A and 7B. Both in FIG. 7A and FIG. 7B, a two-dimensional area is shown in an orthogonal xy system. The vertical axis depicts y in mm, the horizontal axis depicts x in mm. The probe PR2 is positioned in the origin 0,0 and the four electrodes Ei1 to Ei4 are arranged symmetrically on the surface of the probe PR2. FIG. 7A shows the AF profile FS1 for a symmetric field distribution and the AF profile AF3 for an asymmetrical field distribution with directivity along the x axis. FIG. 7B shows the AF profile FS1, AF4, for a symmetric field distribution and an asymmetrical field distribution with directivity in a direction not parallel to the x-axis or the y-axis, respectively. It has to be noted that the AF distribution is also referred to as a field distribution. Both in FIGS. 7A and 7B is provided a DBS device PR2 with an array of 64 stimulation elements implanted in a patient's brain. Further there is provided an UI (User Interface 4 in FIG. 4) to control the stimulation parameters of the DBS device PR2. The UI 4 has an element that allows controlling 'steering' and it has an element that allows controlling 'stimulation spread'. As an example, a user selects two adjacent rings of in total 8 electrodes and defines two 'preferential' electrodes EP above each other and the six other electrodes as 'other' electrodes EO. As a starting point a uniform stimulation spread of 3 mm is used as is indicated in FIGS. 7A and 7B by the areas within the circles FS1 belonging to a symmetrical field distribution. When controlling the 'steering'-function on the UI, we would like to achieve that the spread of stimulation in the preferential direction is constant as function of steering parameters (stays fixed at 3 mm). From simulations we find that if we take $f(\beta)=\frac{1}{3}$, or equivalently $g(\beta)=(1-0.5\beta)$, this can be achieved. Similarly, for $n_{other}=4$ and $n_{pref}=4$ we find that for $f(\beta)=0.5$, or equivalently $g(\beta)=(1-0.25\beta)$, a constant stimulation spread in the preferential direction can be achieved. As an additional effect we observe that the power consumption is much less than for conventional current-steering. This is a consequence of the fact that the current Si supplied to the electrodes Ei is decreased when applying steering. FIG. 7A shows an orthogonal asymmetric field distribution AF3 and FIG. 7B shows a diagonal asymmetric field distribution AF4. FIG. 7C shows a normalized power NP as function of the current-steering balance parameter β in both situations. The dashed line NP3 indicates the power for the diagonal asymmetric field distribution shown in FIG. 7A, the line NP4 shows the power for the orthogonal asymmetric field distribution shown in FIG. 7B.

Constant Power Mode Embodiment

Assume a 64-element stimulation probe PR2 connected to a pulse generator 1 that also provides a large return electrode. The 64×64 matrix R of the stimulation probe is determined by using impedance measurement techniques. Diagonal elements $R_{n,n}$ reflect an electrical impedance from electrode n to the return electrode and off-diagonal elements $R_{m,n}$ correspond to the electrical impedance between elements m and n. The resistance matrix allows computing the 1×64 vector of element voltages $v_i$ (the electrical signals Si of FIG. 4) associated to a distribution of stimulation currents $i_1 \ldots i_{64}$ (the electrical stimulation currents ISi of FIG. 1B) delivered to the 64 elements:

$$\begin{bmatrix} v_1 \\ v_2 \\ v_3 \\ \ldots \\ v_{64} \end{bmatrix} = \begin{bmatrix} R_{1,1} & R_{2,1} & R_{3,1} & \ldots & R_{64,1} \\ R_{1,2} & R_{2,2} & R_{3,2} & \ldots & \ldots \\ R_{1,3} & R_{2,3} & R_{3,3} & \ldots & \ldots \\ \ldots & \ldots & \ldots & \ldots & \ldots \\ R_{1,64} & \ldots & \ldots & \ldots & R_{64,64} \end{bmatrix} * \begin{bmatrix} i_1 \\ i_2 \\ i_3 \\ \ldots \\ i_{64} \end{bmatrix}. \quad (10)$$

The power consumption is obtained by the dot product $$P=V_{el}^T \cdot I=(R \cdot I)^T \cdot I=I^T \cdot R^T \cdot I \quad (11)$$

In constant-power steering mode the dot-product $I^T \cdot R^T \cdot I$ is kept constant.

For example for a symmetric arrangement of 4 electrodes Ei, the power consumption is computed as:

$$P = i_1 * (R_{1,1}*i_1 + R_{2,1}*i_2 + R_{3,1}*i_3 + R_{4,1}*i_4) + \\ \ldots + i_2 * (R_{1,2}*i_1 + R_{2,2}*i_2 + R_{3,2}*i_3 + R_{4,2}*i_4) + \\ \ldots + i_3 * (R_{1,3}*i_1 + R_{2,3}*i_2 + R_{3,3}*i_3 + R_{4,3}*i_4) + \\ \ldots + i_4 * (R_{1,4}*i_1 + R_{2,4}*i_2 + R_{3,4}*i_3 + R_{4,4}*i_4) \quad (12)$$

after substitution for $i_1, i_2, i_3, i_4$ of respectively $i_p, i_o, i_o, i_o$:

$$P=\beta^2 \cdot Tpp + i_o^2 \cdot Too + i_p \cdot i_o \cdot Tpo \quad (13)$$

wherein the terms Tpp, Too, Tpo are sums of some Rij terms of equation (12).

In the symmetric mode, wherein the generated field is symmetrical, holds $i_p=i_o=i_{sym}$ which results in a nominal power of:

$$P_{nom}=i_{sym}^2 \cdot (Tpp+Too+Tpo) \quad (14)$$

Let us assume that in the asymmetric mode holds $i_o=i_{sym} \cdot (1-\beta)$ and $i_p=i_{sym} \cdot f(\beta)$ and that the power in the asymmetric mode should be equal to the power in the symmetric mode, thus:

$$P=(i_{sym} \cdot f(\beta))^2 \cdot Tpp + (i_{sym} \cdot (1-\beta))^2 \cdot Too + i_{sym} \cdot f(\beta) \cdot i_{sym} \cdot (1-\beta) \cdot Tpo \quad (15)$$

This is a second order equation with the unknown $i_p$ which is a function of β. The solution of such an equation can be plotted and then fitted with a second order (or higher order) polynomial. In this manner, the coefficients of the polynomial can be easily determined.

It was found for a second order fitting that $$i_p=i_{sym} \cdot (1.1+2.2 \cdot \beta - 0.95 \cdot \beta^2) \quad (16)$$

If an even more constant power is required, it would of course be possible to more accurately define the function of the current-steering balance parameter β. Although the equation to be solved becomes more complex if more than 4 electrodes are involved, normal algebraic methods can be implemented to find the function of the current-steering balance parameter β.

In another example, for a given symmetric stimulation profile of 4 sites Ei (e.g. sites or electrodes Ei1 to Ei4) each will receive a current Inominal/4, i.e. this corresponds to a current vector $[I_{nominal}/4, I_{nominal}/4, I_{nominal}/4, I_{nominal}/4, 0, \ldots 0]$ and an associated voltage vector computed according to above equation. The power consumption is computed as $$P_{nominal} = i_1 * (R_{1,1} * i_1 + R_{2,1} * i_2 + R_{3,1} * i_3 + R_{4,1} * i_4) + \quad (17)$$
$$\ldots + i_2 * (R_{1,2} * i_1 + R_{2,2} * i_2 + R_{3,2} * i_3 + R_{4,2} * i_4) +$$
$$\ldots + i_3 * (R_{1,3} * i_1 + R_{2,3} * i_2 + R_{3,3} * i_3 + R_{4,3} * i_4) +$$
$$\ldots + i_4 * (R_{1,4} * i_1 + R_{2,4} * i_2 + R_{3,4} * i_3 + R_{4,4} * i_4)$$
$$= (I_{nominal})^2 / 16 * (R_{1,1} + R_{2,1} + R_{3,1} + R_{4,1} + R_{1,2} + \ldots R_{4,1}).$$

Similarly, we can compute $$\overline{I}_{nominal} \cdot \overline{I}_{nominal} = 4*(I_{nominal})^2 / 16 = (I_{nominal})^2 / 4 \quad (18)$$

Now let us assume we wish to perform current steering into one particular direction, namely in the direction associated to stimulation element Ei1. Preferential element Ei1 then receives a current $$i_1 = I_{nom}/4 * (1+3\beta) * g(\beta) \quad (19)$$

wherein $i_1$ corresponds with $i_{pref}$ of equation (8), and stimulation elements Ei2, Ei3, and Ei4 each receive a current $$i_2 = i_3 = i_4 = I_{nom}/4 * (1-\beta) * g(\beta) \quad (20)$$

whereby $i_2$, $i_3$ and $i_4$ correspond with $i_{other}$ of equation (9) and where $g(\beta) < 1$ for $\beta > 0$ according as explained previously. Now we can compute the required $g(\beta)$ in order to achieve the following product constant:

$$\overline{I}_{steer} \cdot \overline{I}_{steer} = (I_{nom})^2 / 16 * (g(\beta))^2 * ((1+3\beta)^2 + 3*(1-\beta)^2) \quad (21)$$

This leads to $$g(\beta) = 2/(4+12\beta^2)^{1/2}$$

The above example can be generalized to the case with $n_{other}$ and $n_{pref}$ electrodes.

Constant Stimulation Spread Mode Embodiment

One way to determine (simulate) stimulation spread is by evaluation of the so-called activating function AF which is the discrete second spatial derivative of the stimulation voltage 3D profile in the tissue $V_t$, see equation (2). If we want to achieve constant stimulation spread into a particular direction this is (approximately) achieved by stating that the activating function AF in a particular direction and at a particular point should stay constant when steering the directivity of the field Fi.

Figure 8B:
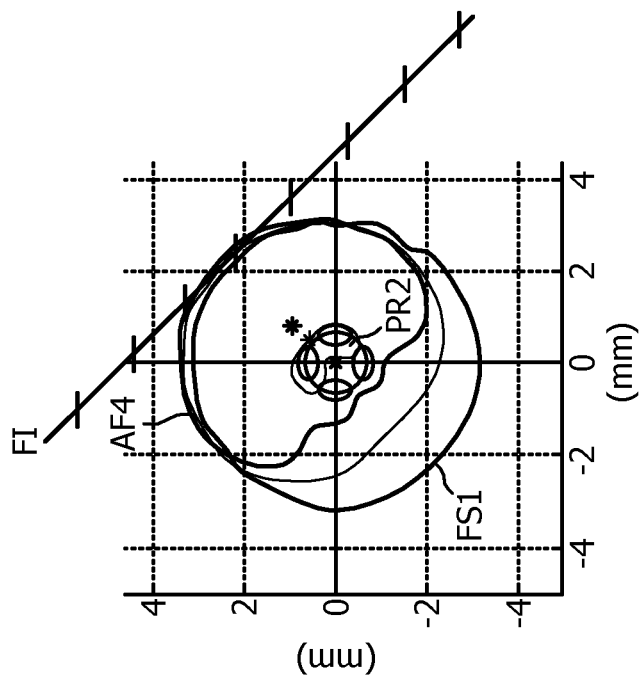
Figure 8A:
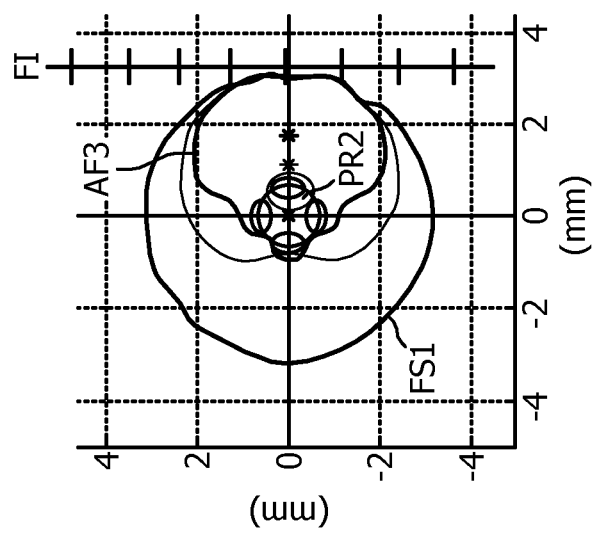

FIGS. 8A and 8B elucidate the spread of a field distribution. Both in FIG. 8A and FIG. 8B, a two-dimensional area is shown in an orthogonal xy system. The vertical axis depicts y in mm, the horizontal axis depicts x in mm. The probe PR2 is positioned in the origin 0,0 and the four electrodes E1 to E4 are arranged symmetrically on the surface of the probe PR2. FIG. 8A shows a symmetric area FS1 and an asymmetrical area AF3 with directivity along the x axis. FIG. 8B shows the symmetric area FS1 and an asymmetrical area AF4 with directivity in a direction not parallel to the x-axis or the y-axis. The thick black line FI indicates the furthest fiber to be activated. It has to be noted that all fibers which cross the areas indicated by FS1 or AF4 will be activated.

Although the areas shown in FIGS. 8A and 8B resemble the areas shown in FIGS. 7A and 7B they need not be identical. In FIGS. 7A and 7B the iso-lines of the activation function AF are shown. The activation function AF is a coarse approximation of whether the neural elements will be activated or not. Thus, it is not sure in FIGS. 7A and 7B whether all fibers within the areas will be activated and that all fibers outside the areas will not be activated. The areas shown in FIGS. 8A and 8B are determined empirically or with a more accurate model than the AF, such that all fibers within the areas of FIGS. 8A and 8B are activated while fibers outside these areas are not activated.

The activation of the fiber FI is predicted by mathematical models of neural elements. Some mathematical models are the activation function AF or the Axon cable model. However, any other mathematical model representing the activation of neural elements could be used instead. The tangential fibers FI shown in FIGS. 8A and 8B are the fibers which are furthest away from the probe PR2 which are still activated by the generated field distribution Fi. Both FIGS. 8A and 8B show examples of when the symmetrical field distribution is changed into an asymmetrical distribution (thus into a field distribution which has a directivity). The spread is kept constant because it is the same shown fiber FI which is the furthest away fiber FI which is activated by the field Fi. It has to be noted that the activation field Fi diminishes with respect to the symmetrical field FS1 in the direction opposite to the directivity.

Figure 9:
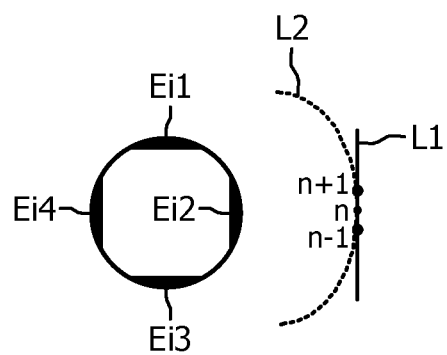
FIG. 9 shows a constant stimulation spread in a tangential direction.

FIG. 9 shows a constant stimulation spread in a tangential direction. At the left side of FIG. 9, the probe PR2 of FIG. 3 is shown. By way of example, let us consider that we want to achieve constant stimulation spread up to a point indicated by n for neuronal elements n−1, n, n+1 running tangentially to the stimulation probe (indicated by the vertical line L1). The dotted line L2 gives an impression of a corresponding (hypothetical) stimulation profile.

To achieve constant stimulation spread in the preferential direction for this particular position n and this particular orientation of neuronal elements n−1, n, n+1 implies that under steering conditions the activating function $AF = V_{n-1} + V_{n+1} - 2*V_n$ should stay constant in point n. Since we have only two parameters to control, namely $\beta$ and $f(\beta)$ (or $g(\beta)$) this cannot be achieved in general (we would need a third control parameter). However, for the present particular example, we can make use of the symmetry of the problem and a solution exists. Since $V_{n-1} = V_{n+1}$, we obtain for the activation function $$AF = 2*(V_{n+1} - V_n) \quad (22)$$

Voltage fields are linearly related to the currents injected through the individual stimulation elements Ei. Let us define $\phi_{n,1}$ and $\phi_{n+1,1}$ as the voltage increments at node n and n+1 respectively that result from unit current delivery through element Ei1. Note that the $\phi$ values can be obtained from simulations (e.g. FEM models) or from measurements (e.g. invasive micro-recordings during stimulation). Likewise, we can obtain such voltage increments for the other stimulation elements Ei2 to Ei4. Then, we obtain as activation function $$AF = 2*i_{pref}*(\phi_{n+1,1} - \phi_{n,1}) + 2*i_{other}*(\phi_{n+1,2} - \phi_{n,2} + \phi_{n+1,3} - \phi_{n,3} + \phi_{n+1,4} - \phi_{n,4}) \quad (23)$$

which under steering conditions shall be kept fixed to a nominal value $AF_{nominal}$. Taking the example where we use $f(\beta)$ for steering correction and after some algebra, this can be rewritten as $$f(\beta) = (K/\beta + \phi_{n+1,2} - \phi_{n,2} + \phi_{n+1,3} - \phi_{n,3} + \phi_{n+1,4} - \phi_{n,4}) / 3(\phi_{n+1,1} - \phi_{n,1}) \quad (24)$$

Again, this is smaller than 1, since the $\phi$ values (and their differences) associated to element Ei1 are larger due to their closer proximity to the element Ei1 as compared to the other elements Ei2 to Ei4. In the limit that point n is infinitely far positioned from the probe PR2, the value of k asymptotes to 1.

It shall be clear that this example can be generalized further by allowing for >2 stimulation current amplitudes and N>2 positions where stimulation voltage should be kept constant.

Figure 10:
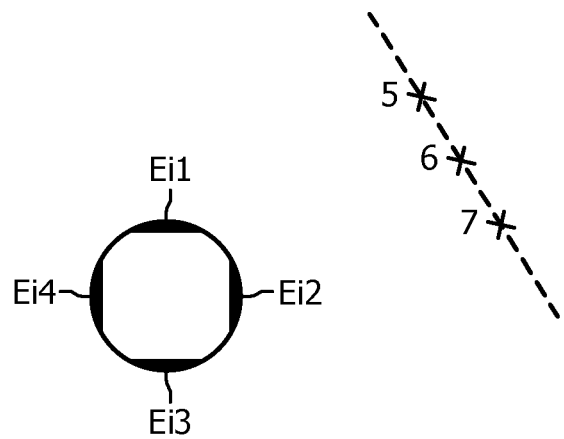
FIG. 10 shows the stimulation spread which is independent on the directivity of the field along a particular section of a fiber arranged in an arbitrary direction.

FIG. 10 shows the stimulation spread which is independent on the directivity of the field along a particular section of a fiber arranged in an arbitrary direction. By way of example, now the situation is considered for an arbitrary direction of the fiber FI. The relevant section of the fiber FI is indicated by the numerals 5, 6 and 7. Further, in this example, the probe has 4 circumferential electrodes which are indicated by the references Ei1 to Ei4 which in the now following are referred to by the indices 1 to 4. According to equation (10), the relation between the voltages on the electrodes Ei and the currents ISi in the tissue wherein the probe PR2 has been inserted is in this example:

$$\begin{bmatrix} v_1 \\ v_2 \\ v_3 \\ \dots \\ v_7 \end{bmatrix} = \begin{bmatrix} R_{1,1} & R_{2,1} & R_{3,1} & \dots & R_{7,1} \\ R_{1,2} & R_{2,2} & R_{3,2} & \dots & \dots \\ R_{1,3} & R_{2,3} & R_{3,3} & \dots & \dots \\ \dots & \dots & \dots & \dots & \dots \\ R_{1,7} & \dots & \dots & \dots & R_{7,7} \end{bmatrix} * \begin{bmatrix} i_1 \\ i_2 \\ i_3 \\ \dots \\ i_7 \end{bmatrix}. \quad (25)$$

wherein $i_5$, $i_6$ and $i_7$ are equal to zero.

The activation function AF for point 6 of the fiber is:

$$AF_{(6)} = v_5 - 2*v_6 + v_7 \quad (26)$$
$$= i_1*(R_{51} - 2*R_{61} + R_{71}) + i_2*(R_{52} - 2*R_{62} + R_{72}) +$$
$$i_3*(R_{53} - 2*R_{63} + R_{73}) + i_4*(R_{54} - 2*R_{64} + R_{74})$$

If is assumed that the current supplied by the preferential electrodes EP is $i_p$ and the current supplied by the other electrodes EO is $i_o$, the activation function AF can be written as:

$$AF_{(6)} = i_p*Tp + i_o*To \quad (27)$$

If the spread should be equal for the symmetrical field distribution FS1 wherein $i_p = i_o = i_{sym}$ and for the asymmetric field distribution AF3 or AF4 wherein $i_o = (1-\beta) i_{sym}$, for the symmetrical field distribution FS1 holds:

$$AF_{(6)} = i_{sym}*(Tp+To) \text{ or } i_{sym} = AF_{(6)}/(Tp+To) \quad (28)$$

and for the asymmetrical field distribution AF3 or AF4 holds according to equations (27) and (28):

$$i_p = (AF_{(6)} - i_o*To)/Tp$$
$$= ((Tp+To)*i_{sym} - (1-\beta)*i_{sym}*To)/(Tp+To) =$$
$$= (1 + \beta*To/Tp)*i_{sym}$$

It should be noted that the above-mentioned embodiments illustrate rather than limit the invention, and that those skilled in the art will be able to design many alternative embodiments without departing from the scope of the appended claims. For example, the probes PR1 and PR2 may have any shape and the electrodes Ei may have any configuration suitable for generating a particular desired field distribution Fi.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for providing an electrical stimulus to surrounding tissue comprising:
    a probe with multiple electrodes forming a high resolution deep brain stimulation array;
    a generator for supplying electrical signals to the electrodes to obtain a field distribution in the surrounding tissue; and
    a controller configured to:
        cause the generator to supply, in a first state, a first distribution of the electrical signals to the electrodes for generating a first field distribution, and
        cause the generator to supply, after supplying the first distribution of the electrical signals to the electrodes and in a second state after gradually changing the distribution of electrical signals from the first state, a second distribution of the electrical signals to the electrodes for generating a second field distribution,
    wherein the first distribution is more symmetrical with respect to the electrodes than the second distribution,
    wherein a sum of electrical stimulation currents generated by the electrical signals in the second state is lower than in the first state, and
    wherein a total power supplied to the electrodes in the first state and in the second state is substantially constant.

2. The system of claim 1, wherein the first field distribution and the second field distribution are distributions of a voltage field, an electrical field, an activating function, or an activation-profile of multi compartment neuronal models.

3. The system of claim 1, wherein the probe has an elongated shape and the multiple electrodes are circumferentially arranged on the probe at different axial positions, wherein several electrodes are present at a same one of the different axial positions.

4. The system of claim 1, further comprising a user interface for inputting a directivity including an orientation of the field distribution.

5. The system of claim 1, further comprising a user interface for inputting a total power supplied to the electrodes.

6. The system of claim 1, further comprising a user interface for inputting a spread of the field distribution.

7. A method of generating an electrical stimulus for application to surrounding tissue with a probe with multiple electrodes forming a high resolution deep brain stimulation array, the method comprising:
    generating electrical signals to obtain a field distribution in the surrounding tissue;
    generating, in a first state, a first distribution of electrical signals for the electrodes to generate a first field distribution; and
    after supplying the first distribution of the electrical signals to the electrodes, generating, in a second state after gradually changing the distribution of electrical signals from the first state, a second distribution of electrical signals for the electrodes to generate a second field distribution, wherein the first distribution is more symmetrical than the second distribution, wherein a total power supplied to the electrodes in the first state and in the second state is substantially constant, and wherein a sum of electrical stimulation currents generated by the electrical signals in the second state is lower than in the first state.

8. A system for providing an electrical stimulus to surrounding tissue comprising:
- a probe with multiple electrodes forming a high resolution deep brain stimulation array;
- a generator for supplying electrical signals to the electrodes to obtain a field distribution in the surrounding tissue; and
- a controller configured to:
  - cause the generator to supply, in a first state, a first distribution of the electrical signals to the electrodes for generating a first field distribution, and
  - cause the generator to supply, after supplying the first distribution of the electrical signals to the electrodes and in a second state after gradually changing the distribution of electrical signals from the first state, a second distribution of the electrical signals to the electrodes for generating a second field distribution,
- wherein the first distribution is more symmetrical with respect to the electrodes than the second distribution,
- wherein a sum of electrical stimulation currents generated by the electrical signals in the second state is lower than in the first state,
- wherein the controller is constructed for adjusting the electrical signals to the electrodes such that the generated field distribution gradually changes from the first field distribution in the first state into the second field distribution in the second state or the other way around, and
- wherein a total power supplied to the electrodes in the first state and in the second state is substantially constant.

9. The system of claim 8, wherein the electrical signals are the electrical stimulation currents, in use, flowing through the electrodes into the surrounding tissue.

10. The system of claim 9, wherein the controller is configured to reduce the sum of electrical stimulation currents to keep the field distribution in the second state within spatial borders of the field distribution in the first state.

11. The system of claim 10, wherein the controller is configured to reduce the sum of electrical stimulation currents to keep a maximum of the field distribution in the second state substantially equal to a maximum of the field distribution in the first state, wherein the maximum of the field distribution is defined by trespassing a threshold of a field strength.

12. The system of claim 8, wherein the probe and the controller are configured to generate, in the first state, a field distribution being symmetrical around the probe and, in the second state, a field distribution having a directivity extending in a desired direction with respect to the probe.

13. A method of providing an electrical stimulus to surrounding tissue comprising:
- providing a probe with multiple electrodes forming a high resolution deep brain stimulation array;
- supplying electrical signals to the electrodes to obtain a field distribution in the surrounding tissue;
- providing, in a first state, a first distribution of the electrical signals to the electrodes for generating a first field distribution, and in a second state after gradually changing the distribution of electrical signals from the first state, a second distribution of the electrical signals to the electrodes for generating a second field distribution; and
- adjusting the electrical signals to the electrodes such that the generated field distribution gradually changes from the first field distribution in the first state into the second field distribution in the second state or the other way around,
- wherein the first distribution is more symmetrical with respect to the electrodes than the second distribution,
- wherein a sum of electrical stimulation currents generated by the electrical signals in the second state is lower than in the first state, and
- wherein a total power supplied to the electrodes in the first state and in the second state is substantially constant.

* * * * *